(12) United States Patent
Gard et al.

(10) Patent No.: US 6,959,248 B2
(45) Date of Patent: Oct. 25, 2005

(54) REAL-TIME DETECTION METHOD AND SYSTEM FOR IDENTIFYING INDIVIDUAL AEROSOL PARTICLES

(75) Inventors: Eric Evan Gard, San Francisco, CA (US); David Philip Fergenson, Livermore, CA (US)

(73) Assignee: The Regents of the University of California, Oakland, CA (US)

(*) Notice: Subject to any disclaimer, the term of this patent is extended or adjusted under 35 U.S.C. 154(b) by 142 days.

(21) Appl. No.: 10/280,608

(22) Filed: Oct. 24, 2002

(65) Prior Publication Data

US 2004/0024539 A1 Feb. 5, 2004

Related U.S. Application Data

(60) Provisional application No. 60/335,598, filed on Oct. 25, 2001.

(51) Int. Cl.[7] .................. G01N 31/00; B01D 59/44
(52) U.S. Cl. ................. 702/22; 702/24; 702/30; 250/285; 250/287
(58) Field of Search .................. 702/19, 22–32; 250/281, 285, 286, 288; 436/173

(56) References Cited

U.S. PATENT DOCUMENTS

| | | | |
|---|---|---|---|
| 4,946,970 A * | 8/1990 | Green et al. .................. 549/245 |
| 5,109,691 A * | 5/1992 | Corrigan et al. ........... 73/23.36 |
| 5,218,529 A | 6/1993 | Meyer | |
| 5,681,752 A | 10/1997 | Prather | |
| 5,798,526 A * | 8/1998 | Shenk et al. ........... 250/339.09 |
| 5,854,676 A * | 12/1998 | Bleuse et al. .............. 356/315 |
| 5,880,830 A * | 3/1999 | Schechter ................. 356/318 |
| 5,900,634 A | 5/1999 | Soloman | |
| 5,946,640 A | 8/1999 | Goodacre et al. | |
| 5,998,215 A * | 12/1999 | Prather et al. .............. 436/173 |
| 6,091,843 A | 7/2000 | Horesh et al. | |
| 6,259,101 B1 | 7/2001 | Wexler et al. | |
| 6,266,390 B1 * | 7/2001 | Sommer et al. ............. 378/45 |
| 6,490,530 B1 * | 12/2002 | Wyatt ........................ 702/24 |

FOREIGN PATENT DOCUMENTS

| | | |
|---|---|---|
| EP | 0 909 426 B1 | 7/2001 |
| WO | WO 01/88531 A1 | 11/2001 |
| WO | WO 01/93307 A2 | 12/2001 |

OTHER PUBLICATIONS

Xin-Hua Song et al, Classification of Single Particles Analyzed by ATOFMS using an Artificial Neural Network, ART-2A, Anal. Chem. 1999 vol. 71, No. 4 Feb. 1999.

(Continued)

*Primary Examiner*—Marc S. Hoff
*Assistant Examiner*—Manuel L. Barbee
(74) *Attorney, Agent, or Firm*—James S. Tak; Alan H. Thompson (57) ABSTRACT

A method and system of identifying individual aerosol particles in real time. Sample aerosol particles are compared against and identified with substantially matching known particle types by producing positive and negative test spectra of an individual aerosol particle using a bipolar single particle mass spectrometer. Each test spectrum is compared to spectra of the same respective polarity in a database of predetermined positive and negative spectra for known particle types and a set of substantially matching spectra is obtained. Finally the identity of the individual aerosol particle is determined from the set of substantially matching spectra by determining a best matching one of the known particle types having both a substantially matching positive spectrum and a substantially matching negative spectrum associated with the best matching known particle type.

45 Claims, 9 Drawing Sheets

OTHER PUBLICATIONS

A. Trimborn et al, Online Analysis of Atmospheric Particles with a Transportable Laser Mass Spectrometer, Aerosol Science and Technology 33:191-201 (2000).

Eric E. Gard et al, Real-time analysis of Individual Atmospheric Aerosol Particles: Design and Performance of a Portable ATOFMS, Anal. Chem. 1997 vol. 69 pp. 4083-4091.

Phillip V. Tan et al, Chemically-Assigned Classification of Aerosol Mass Spectra, American Society for Mass Spectrometry 2002 vol. 13, 826-838.

D. T. Suess et al, Mass spectrometry of Aerosols, Chem. Rev. 1999 vol. 99 pp. 3007-3035.

* cited by examiner

Clostridium Added

- Bacillus Spores
- Clostridium Spores
- Fungal Spores
- Growth Medium
- Gelatin
- Equal
- Gold Bond
- Other

3%
1%
5%

Fig. 9

REAL-TIME DETECTION METHOD AND SYSTEM FOR IDENTIFYING INDIVIDUAL AEROSOL PARTICLES

CLAIM OF PRIORITY IN PROVISIONAL APPLICATION

This application claims priority in provisional application filed on Oct. 25, 2001, entitled "General Aerosol Rapid Detection System" Ser. No. 60/335,598 by inventors Eric E. Gard and David P. Fergenson.

The United States Government has rights in this invention pursuant to Contract No. W-7405-ENG-48 between the United States Department of Energy and the University of California for the operation of Lawrence Livermore National Laboratory.

FIELD OF THE INVENTION

The present invention relates to particle detection systems and methods of analysis. The invention relates more particularly to a rapid detection method and system for determining the identity in real time of individual aerosol particles by comparing bipolar test spectra per individual particle to a database of known particle types, such as biological and chemical threat agents.

BACKGROUND OF THE INVENTION

The potential threat of biological and chemical agent warfare is an ever-increasing national security concern. Of the known biological and chemical warfare agents it has been suggested that those capable of being deployed as aerosols are of greatest concern. Four of the five Centers for Diseases Control and Prevention Category A bioterrorism agents are capable of being transmitted as bio-aerosols, including *Bacillus anthracis*, more commonly known as "anthrax." Unfortunately, the detection of such biological attacks is inherently difficult due to the small sample sizes. For example, a lethal dose of Bacillus anthracis spores weighs only 4 ng. In addition, these small samples can be widely dispersed within the air and may be found mixed with many other aerosol particles present in concentrations thousands of times larger than the bio-aerosol of interest. These demanding sampling conditions and other detection issues such as the unreliability of real time particle source analysis, let alone identification, have been problematic for the rapid screening of packages, letters, baggage, passengers, and shipping containers for biological and/or chemical agents.

While various particle detection methods have been and are currently employed, such as PCR or immuno-assay techniques, they are incapable of real-time analysis and onsite identification of particle source, including threat agents. Moreover, many "online" and "real time" particle detection and analysis systems simply provide sorting of spectral data into similar groups (e.g. via fuzzy logic algorithms) for subsequent visual identification by an expert user. Thus, current methods and systems of "real-time" particle detection, analysis and identification may present too substantial a disruption of commerce to be used as a pragmatic alternative. There is therefore a need for a truly real time particle detection system providing rapid or virtually instantaneous identification of a single aerosol particle from among known particle types or sources, and which goes beyond a simple determination of a particle's chemical composition from mass spectra. Moreover, the ability to rapidly detect and screen bio and chemical aerosols within a complex mixture of background particles would aid in the detection and interdiction of bioterrorist attack.

SUMMARY OF THE INVENTION

One aspect of the present invention includes a method of identifying individual aerosol particles in real time comprising: receiving sample aerosol particles; producing positive and negative test spectra of an individual aerosol particle using a bipolar single particle mass spectrometer; comparing each test spectrum to spectra of the same respective polarity in a database of predetermined positive and negative spectra for known particle types to obtain a set of substantially matching spectra; and determining the identity of the individual aerosol particle from the set of substantially matching spectra by determining a best matching one of the known particle types having both a substantially matching positive spectrum and a substantially matching negative spectrum associated therewith from the set.

Another aspect of the present invention includes a method of detecting in real time chemical and/or biological threat agents from a test specimen comprising: placing the test specimen in an enclosure defining a sampling volume; collecting sample aerosol particles from the sampling volume; receiving the sample aerosol particles into a bipolar single particle mass spectrometer; producing positive and negative test spectra of an individual aerosol particle using the bipolar single particle mass spectrometer; comparing each test spectrum to spectra of the same respective polarity in a database of predetermined positive and negative spectra for known particle types including threat agents, to produce a similarity score for each predetermined spectrum and obtain a set of substantially matching spectra based on a predetermined vigilance factor for similarity scores; determining the identity of the individual aerosol particle from the set of substantially matching spectra by determining a best matching one of the known particle types having both a substantially matching positive spectrum and a substantially matching negative spectrum associated therewith from the set, with at least one of the substantially matching positive and negative spectra having the highest order similarity score of all substantially matching spectra of the same respective polarity; and notifying a user upon identifying the individual aerosol particle as a threat agent from the known particle types.

And still another aspect of the present invention includes a system for identifying individual aerosol particles in real time comprising: a bipolar single particle mass spectrometer adapted to receive sample aerosol particles and produce positive and negative test spectra of individual aerosol particles; a data storage medium; a database of predetermined positive and negative spectra for known particle types stored on the data storage medium; and a data processor having a first data processing module adapted to compare each test spectra to spectra of the same respective polarity in the database to obtain a set of substantially matching spectra, and a second data processing module adapted to determine the identity of the individual aerosol particle from the set of substantially matching spectra by determining a best matching one of the known particle types having both a substantially matching positive spectrum and a substantially matching negative spectrum associated therewith from the set.

BRIEF DESCRIPTION OF THE DRAWINGS

The accompanying drawings, which are incorporated into and form a part of the disclosure, are as follows.

DETAILED DESCRIPTION

The present invention is a general aerosol rapid detection (GARD) system and method which interrogates individual aerosol particles in an effort to characterize a sample that might be of interest either scientifically, medically, commercially, or as an indication of a terrorist threat, or in the interest of law enforcement. In particular, the system and method of the present invention serves to achieve more than a simple determination of a particle's chemical composition or further grouping into similar clusters. Instead, the system operates to analyze and positively identify an individual aerosol particle (not in aggregate) of unknown origin from a database of known particle types, with each known particle type associated with both a positive spectrum profile and a negative spectrum profile. Furthermore, the analysis and identification is achieved online and in real time, with the identification results rapidly communicated to a user in a virtually instantaneous manner.

In this manner, the system may be used to characterize and identify particular substances, such as bioterrorist agents and their surrogates, surrogates of plant, animal and human disease-causing microorganisms, cells in various stages of their life cycles, microorganism growth media, illegal drugs and samples likely to be confused with other threat agents by the casual observer. It is appreciated that the present invention may also be used to characterize and identify samples containing explosives or to monitor an industrial process for a detrimental byproduct. And other applications may include the monitoring of open air for threat agents, the rapid diagnosis of transmissible disease, the rapid and noninvasive detection of explosives, drugs or biological threat agents in packages, envelopes or shipping containers, the rapid biopsy of individual cells for medical diagnoses, real-time building monitoring, and the scientific investigation of single cells and their responses to drugs or other stimuli in cultures, among others.

Figure 1:
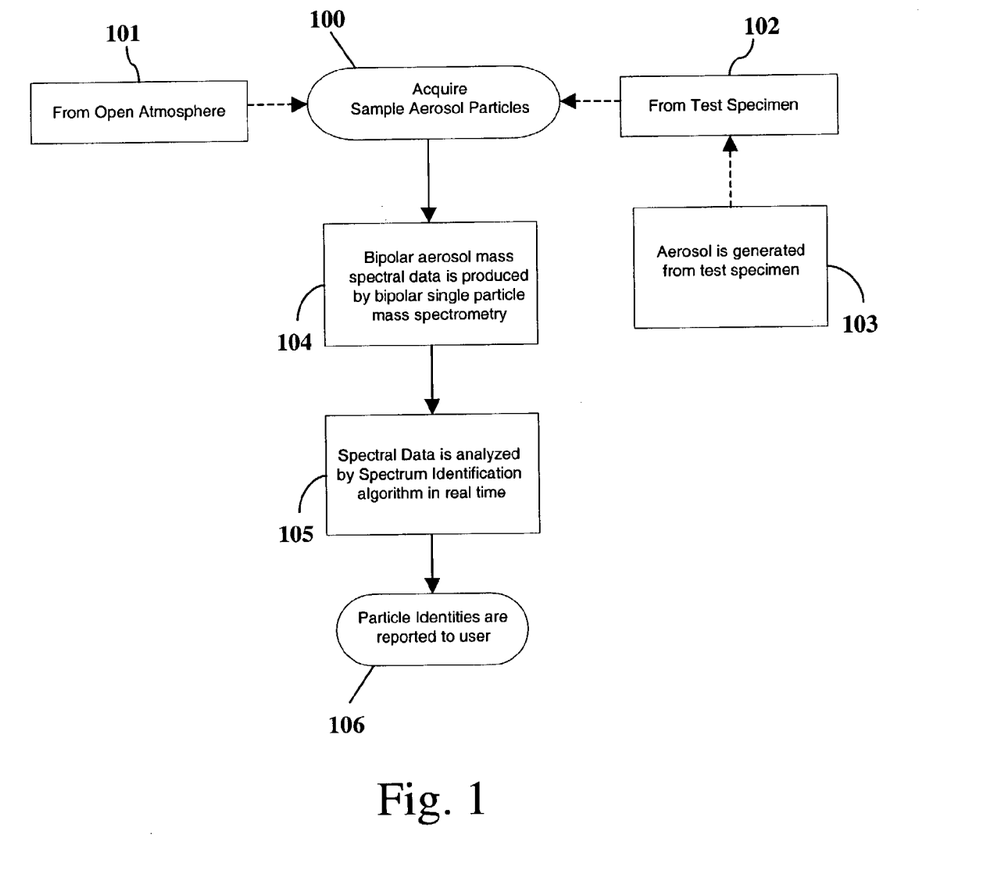
FIG. 1 is an overview flow chart illustrating an exemplary embodiment of the detection method of the present invention.

Turning now to the drawings, FIG. 1 shows an overview flow chart of the various stages of operation of an exemplary embodiment of the detection system and method in accordance with the present invention. The detection method begins at block 100 by collecting or otherwise acquiring sample aerosol particles to be identified. This may be accomplished, for example, using a collection hose or other conduit and a vacuum source (not shown) which together serve to draw the aerosol particles into a mass spectrometer for spectral analysis. It is appreciated that the vacuum source may originate from the mass spectrometer itself or from an external source. In any case, the sample aerosol particles may be acquired from the open atmosphere, as shown at block 101, for open air monitoring applications, or for sampling a volume of space in general, such as a room or an enclosure.

Alternatively, at block 102, sample aerosol particles may also be obtained from a test specimen or other object under inspection (not shown), such as a letter, potentially laden with a threat agent or other target particle type. In contrast to open air monitoring where the particles are already in the aerosol phase, particles must be resuspended from the test specimen for sampling. In this regard, the system may also include an aerosol generator serving to aerosolize particles found on the test specimen. The aerosol generator may operate by blowing compressed air on or in the test specimen to aerosolize and reentrain the particles either from the surface or from within the test specimen. Or aerosol generation may involve the deliberate nebulization of the sample by means of a collision nebulizer or bubble aerosol generator. Alternatively, the aerosol generator may operate by agitating the test specimen, such as by direct manipulation, and then sampling the headspace for aerosol particles that have been resuspended. In any case, once the particles are aerosolized by the aerosol generator, a suitable sample collection apparatus, such as the hose and vacuum arrangement described above, may be utilized for sample collection from the test specimen. It is notable that the test specimen may be first placed within a sampling enclosure serving to restrict generated aerosol particles to within the enclosed sampling volume. And a "test specimen" may be any physical object or sample which is the subject of inspection and testing, including, but not limited to, letters, parcels, containers, baggage, and even people, e.g. airline passengers.

Figure 6:
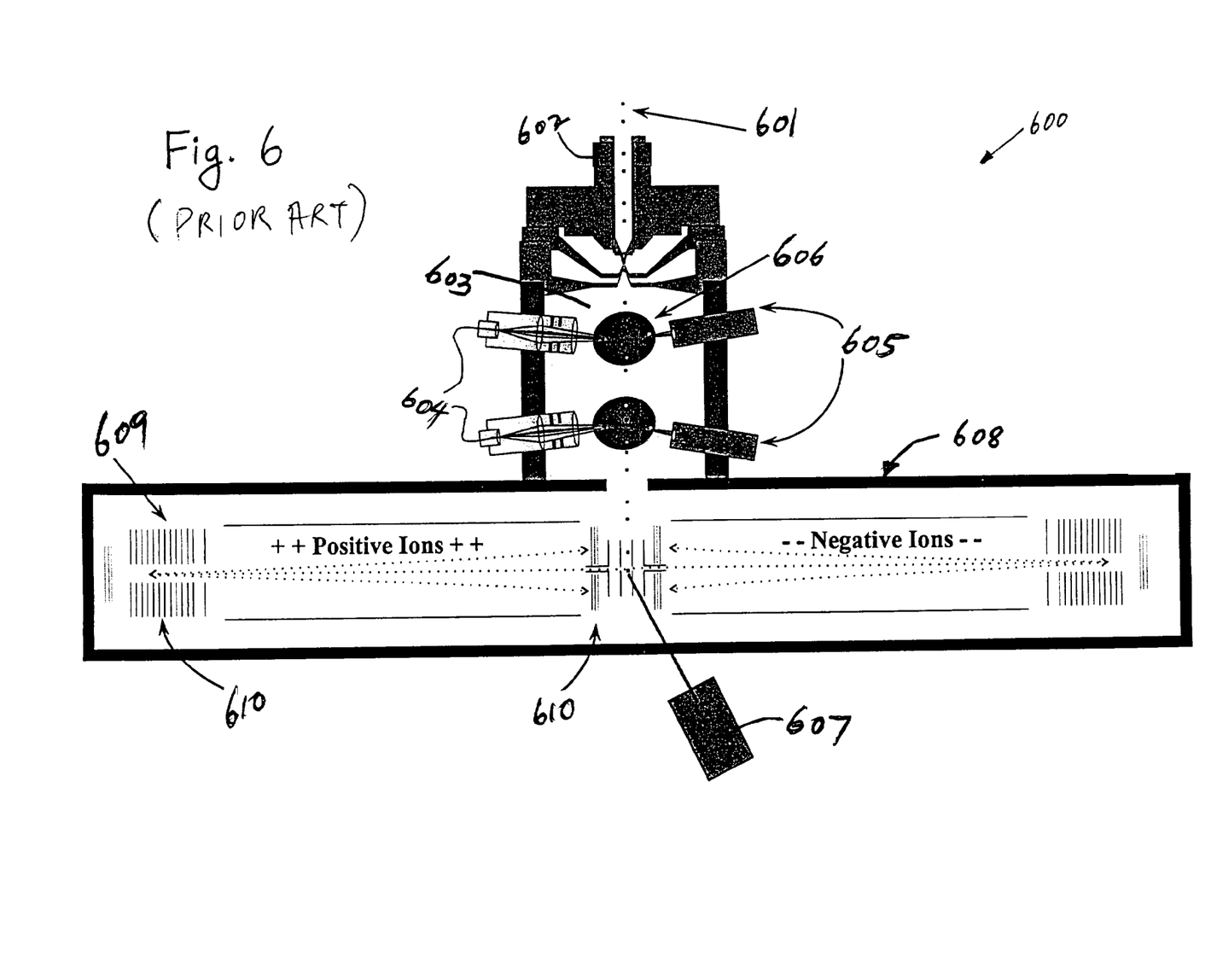
FIG. 6 is a schematic view of an exemplary prior art aerosol time of flight mass spectrometer which may be utilized in the present invention.

Next, at block 104, the acquired sample aerosol particles are transmitted to a bipolar single particle mass spectrometer for spectral analysis, such as an aerosol time-of-flight mass spectrometer (ATOFMS) shown in FIG. 6. FIG. 6 shows an exemplary bipolar ATOFMS, generally indicated at reference character 600, of a type disclosed in U.S. Pat. No. 5,998,215 to Prather et. al incorporated by reference herein. While this ATOFMS is but one type of bipolar single particle mass spectrometer usable in the present invention, the Prather ATOFMS will be referenced hereinafter as a representative bipolar single particle mass spectrometer. As can be seen in FIG. 6, individual aerosol particles 601 enter the ATOFMS though an aerosol inlet port 602 and are supersonically expanded through a nozzle to differentiate the velocities of different sized particles. The individual particles are then passed through a particle sizing region 603 where the aerodynamic diameter of the particles are determined by the size-dependent velocity distribution. This is accomplished by using a pair of lasers 604, such as a continuous-wave argon ion laser beam, from which a passing particle generates a pulse of scattered light. The scattered light is collected by a corresponding one of a pair of photomultiplier tubes 605 (PMT) using elliptical mirrors 606. Particle velocity is determined from the predetermined distance between the two laser beams and the measured time between the two scatter pulses. In this manner, a timing circuit (not shown) tracks an individual particle and controls the firing of a desorption/ionization laser, such as a Nd:Yag laser to generate positive and negative ions at a source region of a laser desorption/ionization time-of-flight mass spectrometer 608. The mass spectrometer 608 has two reflectron-fitted flight tubes 609 capable of processing positive and negative ions. Annular detectors, such as MSP detectors 610, are utilized for detecting the reflected ions and provides a time spectrum of each of the particles to produce both positive and negative mass-to-charge spectra. In this manner, bipolar aerosol mass spectral data is produced by bipolar single particle mass spectroscopy at block 104 of FIG. 1.

Figure 2:
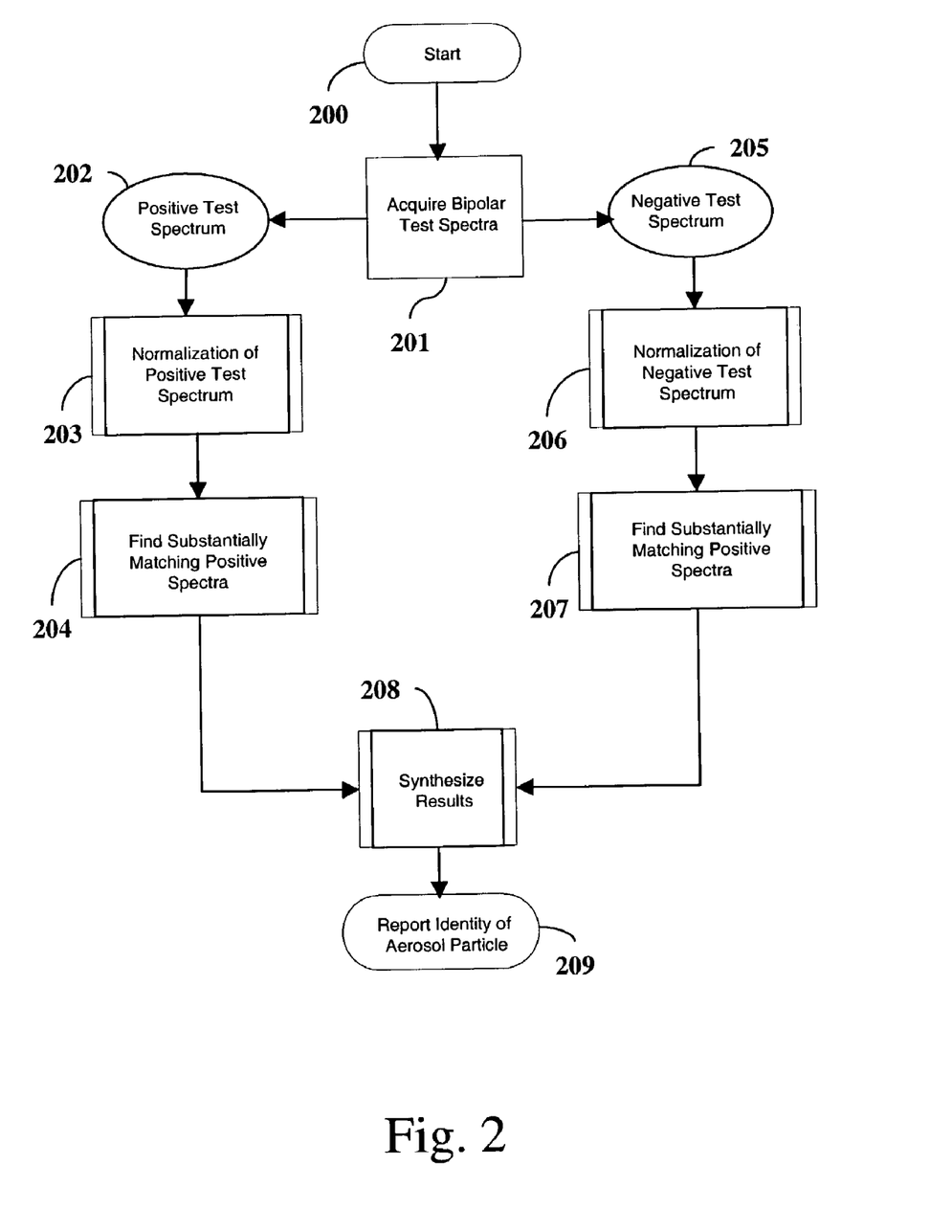
FIG. 2 is an overview flow chart of the spectral identification algorithm.

At block 105 of FIG. 1, the bipolar spectral data produced and acquired by the ATOFMS is analyzed in real time by a data processing system, such as a computer processor, in a spectrum identification algorithm (hereinafter "algorithm") shown in detail in FIGS. 2–5. It is notable that the data processing system need not be in local proximity to the ATOFMS, with spectral data being transmitted to the data processing system via intranet or Internet. FIG. 2 shows an overview flow chart of the steps in the algorithm starting at box 200. Generally the algorithm acquires test spectra at 201 for both positive and negative polarities. The positive test spectrum is analyzed starting at 202, while the negative test spectrum is analyzed starting at 205. However, as can be seen from steps 203 to 207, the analyses of both spectra are processed in parallel. In particular, a preliminary processing step is first encountered at steps 203 and 206 normalizing the respective positive and negative test spectra to vector quantities.

Figure 3:
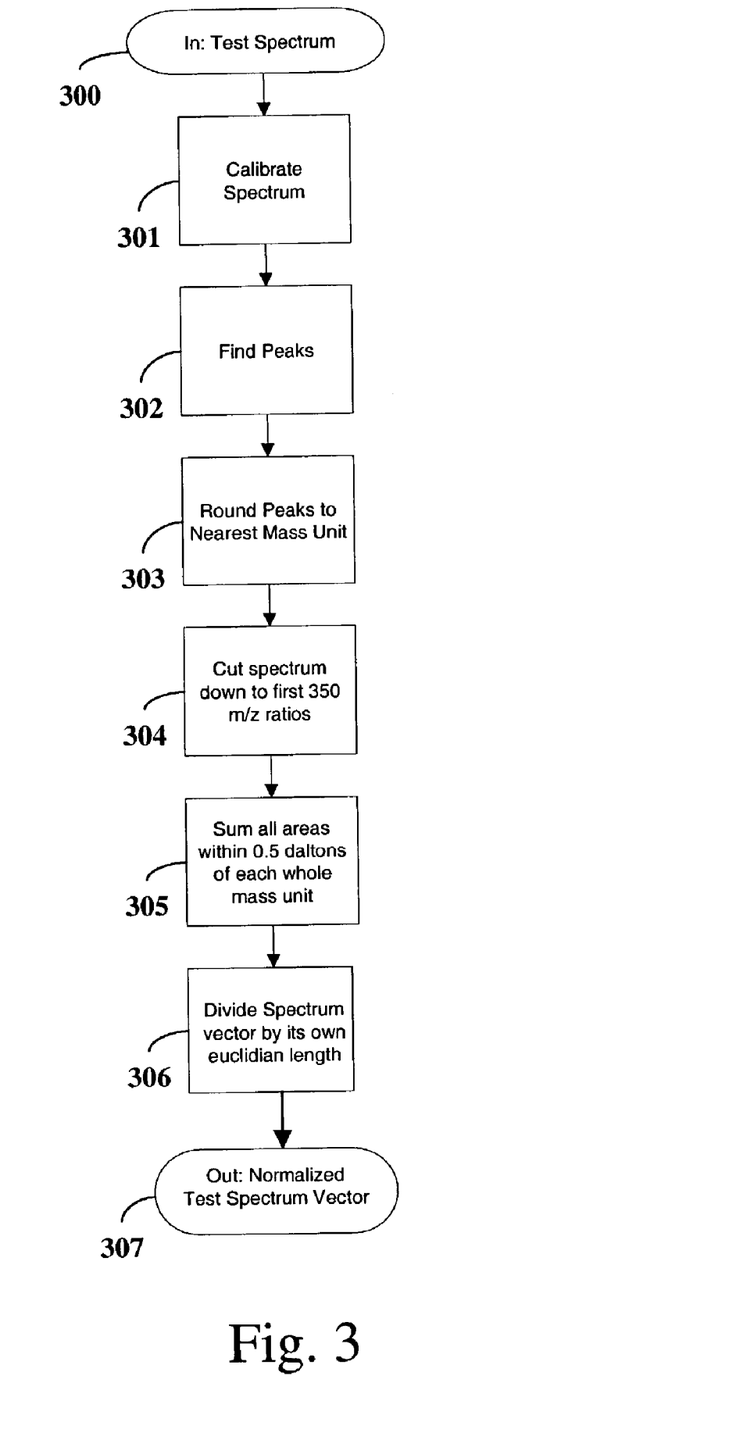
FIG. 3 is a flow chart illustrating an exemplary embodiment of the normalization process of the spectral identification algorithm.

Details of the normalization process for test spectra are shown in FIG. 3, starting at 300 with a subject test spectrum. The normalization procedure may be carried out by a data processing module of the data processing system which is specifically adapted for such a purpose. Examining the normalization of the positive spectral data first, the positive test spectrum is calibrated at step 301. The positive test spectrum is simplified to a vector of preferably double precision real numbers by first finding all peaks below a predetermined maximum m/z, e.g. 350.5, at step 302, and noting their masses and another peak attribute, such as area, height, or width. In an alternative embodiment, only selected peaks based on a predetermined selection criteria may be examined, such as those found within a specified m/z range or window. Next the masses of the peaks are rounded to the nearest whole mass unit at 303. All other peaks not below the maximum m/z are omitted at 304. The areas are summed at 305 where they fall on the same whole mass unit after rounding, and recorded as a vector of real numbers where the nth number corresponds to the combined areas of all peaks within 0.5 mass units of n. At 306, this vector is normalized to unit length by dividing it by its Euclidean length as computed by the Pythagorean theorem. That is, the length is computed by taking the square root of the sum of the squares of each number in the vector, and then each number in the vector is divided by that length. At 307, the normalized positive test spectrum vector is returned. A similar normalization process also occurs for the negative test spectrum to output a normalized negative test spectrum vector.

Following the normalization of the positive test spectrum in step 203 in FIG. 2, the algorithm proceeds to 204 where substantially matching positive spectra are found which substantially match the positive test spectrum. Similarly, substantially matching negative spectra are found at 207 which substantially match the negative test spectrum. The substantially matching procedure may be carried out by a second data processing module of the data processing system which is specifically adapted for such a purpose.

Figure 4:
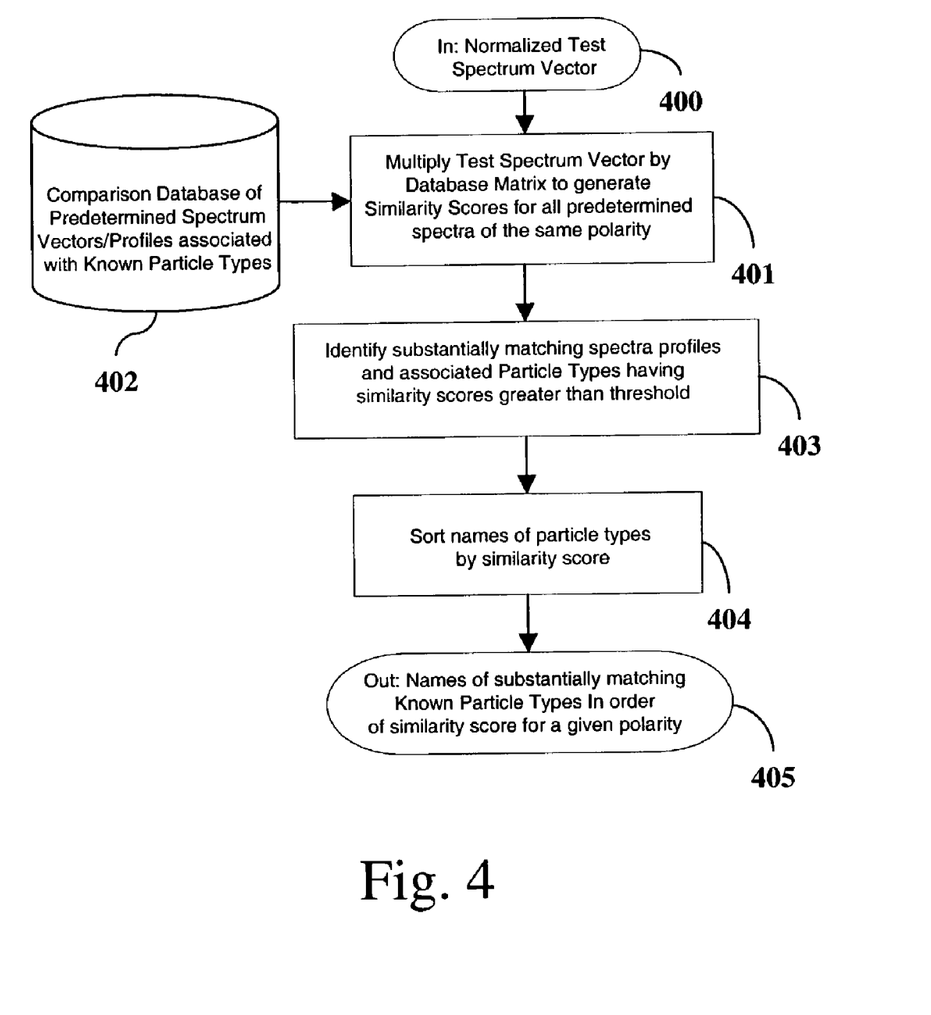
FIG. 4 is a flow chart illustrating an exemplary embodiment of a process for finding substantially matching spectra in the spectral identification algorithm.

Details of the substantially matching process for test spectra are shown in FIG. 4, starting at 400 with a normalized test spectrum vector. Examining first for the normalized positive test spectrum vector, the normalized positive test spectrum vector is compared at 401 to all spectra of the same respective polarity found in a database 402 of predetermined positive and negative spectra for known particle types. Thus the positive test spectrum is compared to all predetermined positive spectra in the database, each associated with a known particle type, e.g. bacillus anthracis. In particular, each of the normalized positive test spectrum vector is multiplied (dot product) by the transpose of each previously defined and scaled (normalized) spectrum vector of the same respective polarity in the database, where each database vector is labeled according to its origin. It is notable that one way to generate these predetermined spectra is by running known standards and simplifying their spectra into vectors. These predetermined standard vectors are then stored in the database, for example, as a vector matrix. In any event, the dot product of each vector multiplication produces a similarity score for all predetermined spectra of the same polarity representing their degrees of similarity on a scale of 0 to 1, with 0 being completely orthogonal and 1 being exactly identical.

Next, at step 403 "substantial similarity" between the test spectra and the database spectra of the same respective polarity is determined from the resulting similarity scores, with the determining criterion for substantial similarity being based on a similarity score threshold, also referred as a vigilance factor. For example, a predetermined positive database spectrum may be determined to be "substantially similar" to the positive test spectrum if the dot product exceeds a predetermined vigilance factor, such as 0.7. In other words, the vigilance factor is considered to be the minimum degree of similarity acceptable to call the test spectrum substantially similar to the standard. And at step 404 the names of the particle types associated with substantially matching database spectra of a given polarity are sorted in order of similarity score, such as in decreasing order, for output at step 405.

Figure 5:
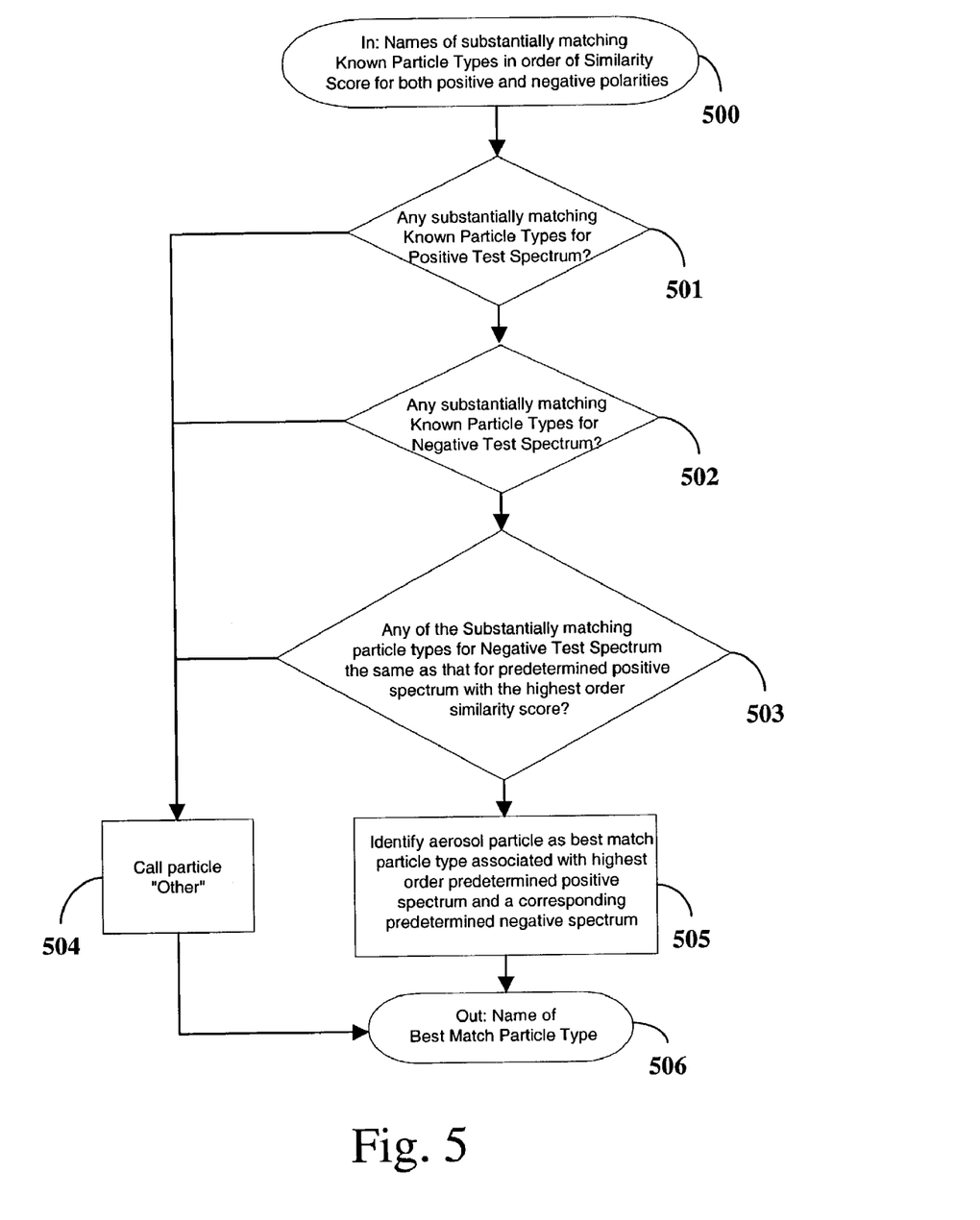
FIG. 5 is a flow chart illustrating an exemplary embodiment of a process for synthesizing results in the spectral identification algorithm.

Following the finding of substantially matching positive and negative spectra at steps 204 and 205, respectively, in FIG. 2 the results from both polarities are synthesized at step 208. FIG. 5 shows the details of an exemplary embodiment of the results synthesis for determining the identity of a single aerosol particle. At 500, the names of substantially matching known particle types in order or similarity score are received as input for both positive and negative polarities. At step 501, a determination is made if any substantially matching known particle types exist for positive spectra. If no, the aerosol particle is called "other" at 504 due to a failed identification. If a substantially matching known particle type is found for positive spectra, then a determination is made at step 502 whether any substantially matching known particle types exist for negative spectra. If no again, the particle is called "other" at 504 and identification for the particular aerosol particle terminates. If however, a substantially matching known particle type is found for negative spectra, then a further determination is made at step 503 whether any of the substantially matching particle types for negative spectra are the same as for the positive spectra with the highest order similarity score. Again, if no, then the particle is called "other" at 504. But if yes, then the aerosol particle is identified as the best matching one of the known particle types associated with the highest order positive spectra and any corresponding negative spectra. The results synthesis module ends with an output of the name of the best match particle type.

Generally, if both polarities "match" spectra profiles with the same particle type, then the test spectrum is identified as that particle type, i.e. assigned that particle label. In situations encountering multiple matches within database spectra of a given polarity, then the best match is considered to be the particle type associated with the highest order similarity score for the positive spectrum that has any corresponding substantial match with the negative spectrum. For example, if there were matches of 0.8 for "Bacillus Spores" and 0.75 for "Growth Medium" for the positive spectrum and matches of 0.9 for "Growth Medium" and 0.75 for "Bacillus Spores" for the negative, then the spectrum would be identified as "Bacillus Spores". If there is no match that matches both polarities, then the particle is labeled "Other".

It is notable here that in the exemplary embodiment of FIG. 5, the aerosol particle is identified with one of the known particle types from the database having associated therewith the highest order similarity score for all positive spectra, while having only a substantial match with a negative spectrum. However, in another exemplary embodiment not shown, an aerosol particle may be identified with one of the known particle types from the database having associated therewith the highest order similarity score for all negative spectra, while having only a substantial match with a positive spectrum. In any case, positive and negative spectra are considered in the identification process.

Figure 7:
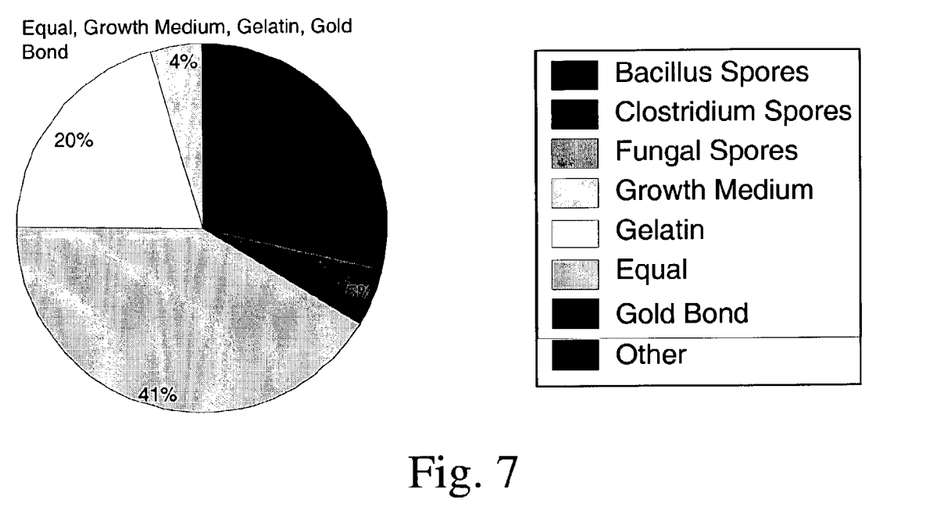
FIG. 7 is a pie chart and legend illustrating the identification results of a first complex mixture.
Figure 8:
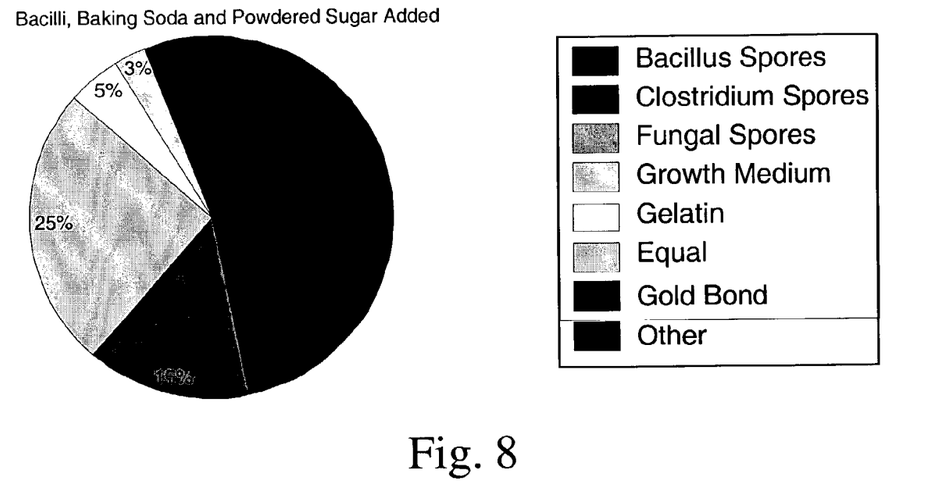
FIG. 8 is a pie chart and legend illustrating the identification results of a second complex mixture with additional substances, including Bacillus spores, added to the first complex mixture of FIG. 7.
Figure 9:
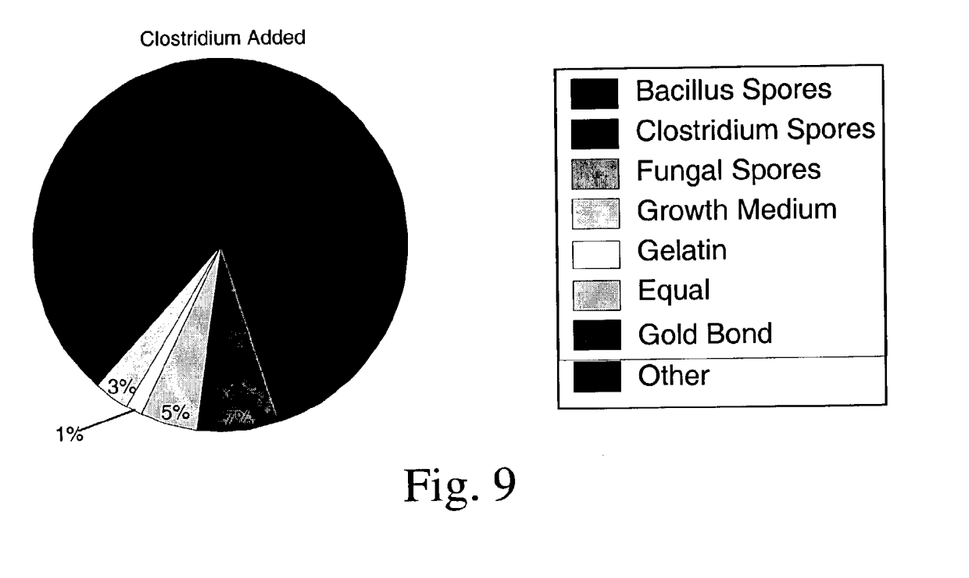
FIG. 9 is a pie chart and legend illustrating the identification results of a third complex mixture with still additional substances, including Clostridium, added to the second complex mixture of FIG. 8.

Upon completion of the spectrum identification algorithm of 105 in FIG. 1, the detection method proceeds to communicate the results to a user in real time. The communication may be a reporting of the aerosol particle identities by visual display, such as on a CRT screen, audio, or other means of notification. A notification signal may particularly be useful in alerting a user to the identification of a particular substance or substances which were targeted in the inspection, such as the detection of biological or chemical threat agents. For the visual reporting of the particle identification, a pie chart, bar graph, or other comparative visualization tool may be utilized, such as shown in FIGS. 7–9, indicating particles types and concentrations thereof. In one embodiment, the visual display would prioritize the most serious threats for display in a more prominent location than routine particles. In any case, the results are presented to a user automatically, and virtually instantaneously, while spectral analysis proceeds.

FIGS. 7–9 illustrate the detection results of an experiment conducted by Applicants to demonstrate the present invention's ability for detecting bacterial spores, e.g. Bacillus spores, in a complex mixture. FIG. 7 shows a first mixture of non-biological test samples, absent Bacillus spores. And FIG. 8 shows the same mixture of FIG. 7 with Bacillus spores added, as well as two previously uncharacterized samples of baking soda and powdered sugar. Furthermore, FIG. 9 shows the mixture of FIG. 8 with Clostridium spores nebulized into the sample. As can be seen in FIGS. 8 and 9, Bacillus spores were detected by the present invention even for Bacillus spore concentrations at 6% and 4% respectively.

While particular operational sequences, materials, temperatures, parameters, and particular embodiments have been described and or illustrated, such are not intended to be limiting. Modifications and changes may become apparent to those skilled in the art, and it is intended that the invention be limited only by the scope of the appended claims.

We claim:

1. A method of identifying individual aerosol particles in real time comprising:
   receiving sample aerosol particles;
   producing positive and negative test spectra of an individual aerosol particle using a bipolar single particle mass spectrometer;
   comparing each test spectrum to spectra of the same respective polarity in a database of predetermined positive and negative spectra for known particle types to obtain a set of substantially matching spectra; and
   determining the identity of the individual aerosol particle from the set of substantially matching spectra by determining a best matching one of the known particle types having both a substantially matching positive spectrum and a substantially matching negative spectrum associated therewith from the set.

2. The method as in claim 1,
   wherein the comparison of each test spectrum to spectra of the same respective polarity in the database produces a similarity score for each predetermined spectrum, with the set of substantially matching spectra based on a predetermined similarity score threshold.

3. The method as in claim 2,
   wherein the best matching one of the known particle types has associated therewith, for at least one of the substantially matching positive and negative spectra, the highest order similarity score of all substantially matching spectra of the same respective polarity.

4. The method as in claim 2,
   wherein the comparison of each test spectrum to the database includes converting each test spectrum into a corresponding test spectrum vector, and vector multiplying the test spectrum vector with a transpose of a predetermined spectrum vector of the same respective polarity to calculate the similarity score.

5. The method as in claim 1,
   wherein the sample aerosol particles are received from the open atmosphere.

6. The method as in claim 1,
   wherein the sample aerosol particles are from a test specimen.

7. The method as in claim 6,
   wherein the sample aerosol particles are received from a sampling volume containing the test specimen.

8. The method as in claim 6,
   further comprising generating the sample aerosol particles from the test specimen.

9. The method as in claim 8,
   wherein the sample aerosol particles are generated by blowing air on the test specimen.

10. The method as in claim 8,
    wherein the sample aerosol particles are generated by agitating the test specimen.

11. The method as in claim 1,
    further comprising communicating to a user in real time the identity determination of the individual aerosol particle.

12. The method as in claim 11,
wherein the real time communication includes notifying the user when a specific known particle type is identified.

13. The method as in claim 11,
wherein the real time communication includes notifying the user when a specific chemical composition is identified.

14. The method as in claim 11,
wherein the real time communication includes displaying the identity determination to the user.

15. The method as in claim 14,
wherein the displayed identity determination indicates concentration level of the identified individual aerosol particle with respect to all analyzed sample aerosol particles.

16. The method as in claim 1,
wherein the bipolar single particle mass spectrometer is an aerosol time-of-flight mass spectrometer.

17. A method of detecting in real time chemical and/or biological threat agents from a test specimen comprising:
placing the test specimen in an enclosure defining a sampling volume;
collecting sample aerosol particles from the sampling volume;
receiving the sample aerosol particles into a bipolar single particle mass spectrometer;
producing positive and negative test spectra of an individual aerosol particle using the bipolar single particle mass spectrometer;
comparing each test spectrum to spectra of the same respective polarity in a database of predetermined positive and negative spectra for known particle types including threat agents, to produce a similarity score for each predetermined spectrum and obtain a set of substantially matching spectra based on a predetermined similarity score threshold;
determining the identity of the individual aerosol particle from the set of substantially matching spectra by determining a best matching one of the known particle types having both a substantially matching positive spectrum and a substantially matching negative spectrum associated therewith from the set, with at least one of the substantially matching positive and negative spectra having the highest order similarity score of all substantially matching spectra of the same respective polarity; and
notifying a user upon identifying the individual aerosol particle as a threat agent from the known particle types.

18. The method as in claim 17,
wherein the comparison of each test spectrum to the database includes converting each test spectrum into a corresponding test spectrum vector, and vector multiplying the test spectrum vector with a transpose of a predetermined spectrum vector of the same respective polarity to calculate the similarity score.

19. The method as in claim 17,
further comprising generating the sample aerosol particles from test specimen into the sampling volume.

20. The method as in claim 19,
wherein the sample aerosol particles are generated by blowing air on the test specimen.

21. The method as in claim 19,
wherein the sample aerosol particles are generated by agitating the test specimen.

22. The method as in claim 17,
wherein the user notification includes displaying the identity determination of the threat agent to the user.

23. The method as in claim 22,
wherein the displayed identity determination indicates concentration level of the identified threat agent with respect to all analyzed sample aerosol particles.

24. A system for identifying individual aerosol particles in real time comprising:
a bipolar single particle mass spectrometer adapted to receive sample aerosol particles and produce positive and negative test spectra of individual aerosol particles;
a data storage medium;
a database of predetermined positive and negative spectra for known particle types stored on the data storage medium; and
a data processor having a first data processing module adapted to compare each test spectra to spectra of the same respective polarity in the database to obtain a set of substantially matching spectra, and a second data processing module adapted to determine the identity of the individual aerosol particle from the set of substantially matching spectra by determining a best matching one of the known particle types having both a substantially matching positive spectrum and a substantially matching negative spectrum associated therewith from the set.

25. The system as in claim 24,
wherein the first data processing module produces a similarity score for each comparison of the respective test spectra to the database of predetermined positive and negative spectra, and determines the set of substantially matching spectra based on a predetermined similarity score threshold.

26. The system as in claim 25,
wherein the best matching one of the known particle types has associated therewith, for at least one of the substantially matching positive and negative spectra, the highest order similarity score of all substantially matching spectra of the same respective polarity.

27. The system as in claim 24,
wherein the first data processing module is adapted to convert each test spectrum into a corresponding test spectrum vector, and vector multiply the test spectrum vector with a transpose of a predetermined spectrum vector of the same respective polarity to calculate the similarity score.

28. The system as in claim 24,
further comprising means for collecting the sample aerosol particles from the open atmosphere.

29. The system as in claim 24,
further comprising means for collecting the sample aerosol particles from a test specimen.

30. The system as in claim 29,
further comprising an enclosure defining a sampling volume for receiving the test specimen, wherein the sample aerosol particles are collected from the sampling volume.

31. The system as in claim 29,
further comprising an aerosol generator for generating the sample aerosol particles from the test specimen.

32. The system as in claim 31,
wherein the aerosol generator is adapted to blow air on the test specimen.

33. The system as in claim 31,
wherein the aerosol generator is adapted to agitate the test specimen.

34. The system as in claim 24,
further comprising means for communicating to a user in real time the identity of the individual aerosol particle.

35. The system as in claim 34,
wherein the means for real time communication notifies the user when a specific known particle type is identified.

36. The system as in claim 34,
wherein the means for real time communication notifies the user when a specific chemical composition is identified.

37. The system as in claim 34,
wherein the means for real time communication displays the identity determination to the user.

38. The system as in claim 37,
wherein the displayed identity determination indicates concentration level of the identified individual aerosol particle with respect to all analyzed sample aerosol particles.

39. The system as in claim 24,
wherein the bipolar single particle mass spectrometer is an aerosol time-of-flight mass spectrometer.

40. A method of identifying individual aerosol particles in real time comprising:
receiving sample aerosol particles;
producing positive and negative test spectra of an individual aerosol particle using a bipolar single particle mass spectrometer;
comparing each test spectrum to spectra of the same respective polarity in a database of predetermined positive and negative spectra for known particle types so that a similarity score is produced for each predetermined spectrum anc a set of substantially matching spectra is obtained based on a predetermined similarity score threshold; and
determining the identity of the individual aerosol particle from the set of substantially matching spectra by determining a best matching one of the known particle types having both a substantially matching positive spectrum and a substantially matching negative spectrum associated therewith from the set, wherein the best matching one of the known particle types has associated therewith a substantially matching positive spectrum with the highest order similarity score of all substantially matching positive spectra.

41. A method of identifying individual aerosol particles in real time comprising:
receiving sample aerosol particles;
producing positive and negative test spectra of an individual aerosol particle using a bipolar single particle mass spectrometer;
comparing each test spectrum to spectra of the same respective polarity in a database of predetermined positive and negative spectra for known particle types so that a similarity score is produced for each predetermined spectrum and a set of substantially matching spectra is obtained based on a predetermined similarity score threshold; and
determining the identity of the individual aerosol particle from the set of substantially matching spectra by determining a best matching one of the known particle types having both a substantially matching positive spectrum and a substantially matching negative spectrum associated therewith from the set, wherein the best matching one of the known particle types has associated therewith a substantially matching negative spectrum with the highest order similarity score of all substantially matching negative spectra.

42. A method of detecting in real time chemical and/or biological threat agents from a test specimen comprising:
placing the test specimen in an enclosure defining a sampling volume;
collecting sample aerosol particles from the sampling volume;
receiving the sample aerosol particles into a bipolar single particle mass spectrometer;
producing positive and negative test spectra of an individual aerosol particle using the bipolar single particle mass spectrometer;
comparing each test spectrum to spectra of the same respective polarity in a database of predetermined positive and negative spectra for known particle types including threat agents, to produce a similarity score for each predetermined spectrum and obtain a set of substantially matching spectra based on a predetermined similarity score threshold;
determining the identity of the individual aerosol particle from the set of substantially matching spectra by determining a best matching one of the known particle types having both a substantially matching positive spectrum and a substantially matching negative spectrum associated therewith from the set, wherein the best matching one of the known particle types has associated therewith a substantially matching positive spectrum with the highest order similarity score of all substantially matching positive spectra; and
notifying a user upon identifying the individual aerosol particle as a threat agent from the known particle types.

43. A method of detecting in real time chemical and/or biological threat agents from a test specimen comprising:
placing the test specimen in an enclosure defining a sampling volume;
collecting sample aerosol particles from the sampling volume;
receiving the sample aerosol particles into a bipolar single particle mass spectrometer;
producing positive and negative test spectra of an individual aerosol particle using the bipolar single particle mass spectrometer;
comparing each test spectrum to spectra of the same respective polarity in a database of predetermined positive and negative spectra for known particle types including threat agents, to produce a similarity score for each predetermined spectrum and obtain a set of substantially matching spectra based on a predetermined similarity score threshold;
determining the identity of the individual aerosol particle from the set of substantially matching spectra by determining a best matching one of the known particle types having both a substantially matching positive spectrum and a substantially matching negative spectrum associated therewith from the set, wherein the best matching one of the known particle types has associated therewith a substantially matching negative spectrum with the highest order similarity score of all substantially matching negative spectra; and
notifying a user upon identifying the individual aerosol particle as a threat agent from the known particle types.

44. A system for identifying individual aerosol particles in real time comprising:
a bipolar single particle mass spectrometer adapted to receive sample aerosol particles and produce positive and negative test spectra of individual aerosol particles;

a data storage medium;

a database of predetermined positive and negative spectra for known particle types stored on the data storage medium; and a data processor having:

a first data processing module adapted to compare each test spectra to spectra of the same respective polarity in the database so that a similarity score is produced for each comparison of the respective test spectra to the database of predetermined positive and negative spectra, and a set of substantially matching spectra is determinably obtained based on a predetermined similarity score threshold; and a second data processing module adapted to determine the identity of the individual aerosol particle from the set of substantially matching spectra by determining a best matching one of the known particle types having both a substantially matching positive spectrum and a substantially matching negative spectrum associated therewith from the set, wherein the best matching one of the known particle types has associated therewith a substantially matching positive spectrum with the highest order similarity score of all substantially matching positive spectra.

45. A system for identifying individual aerosol particles in real time comprising:

a bipolar single particle mass spectrometer adapted to receive sample aerosol particles and produce positive and negative test spectra of individual aerosol particles;

a data storage medium;

a database of predetermined positive and negative spectra for known particle types stored on the data storage medium; and a data processor having:

a first data processing module adapted to compare each test spectra to spectra of the same respective polarity in the database so that a similarity score is produced for each comparison of the respective test spectra to the database of predetermined positive and negative spectra, and a set of substantially matching spectra is determinably obtained based on a predetermined similarity score threshold; and a second data processing module adapted to determine the identity of the individual aerosol particle from the set of substantially matching spectra by determining a best matching one of the known particle types having both a substantially matching positive spectrum and a substantially matching negative spectrum associated therewith from the set, wherein the best matching one of the known particle types has associated therewith a substantially matching negative spectrum with the highest order similarity score of all substantially matching negative spectra.

* * * * *